United States Patent
Neff

[11] Patent Number: 6,165,135
[45] Date of Patent: Dec. 26, 2000

[54] SYSTEM AND METHOD OF INTERROGATING IMPLANTED PASSIVE RESONANT-CIRCUIT DEVICES

[76] Inventor: Samuel R. Neff, 600 Fairview Rd., Narberth, Pa. 19072

[21] Appl. No.: 09/354,385

[22] Filed: Jul. 14, 1999

[51] Int. Cl.[7] ........................................................ A61B 5/00
[52] U.S. Cl. ................................................................ 600/561
[58] Field of Search ........................... 600/561, 587, 600/595; 343/700, 767

[56] References Cited

U.S. PATENT DOCUMENTS

| | | |
|---|---|---|
| 3,774,112 | 11/1973 | Panico . |
| 3,789,667 | 2/1974 | Porter et al. . |
| 3,853,117 | 12/1974 | Murr . |
| 3,943,915 | 3/1976 | Severson . |
| 3,968,491 | 7/1976 | Silberberg . |
| 3,977,391 | 8/1976 | Fleischmann . |
| 4,003,141 | 1/1977 | Le Roy . |
| 4,014,319 | 3/1977 | Favre . |
| 4,026,276 | 5/1977 | Chubbuck . |
| 4,062,354 | 12/1977 | Taylor et al. . |
| 4,114,606 | 9/1978 | Seylar . |
| 4,127,110 | 11/1978 | Bullara . |
| 4,186,749 | 2/1980 | Fryer . |
| 4,206,761 | 6/1980 | Cosman . |
| 4,206,762 | 6/1980 | Cosman . |
| 4,246,908 | 1/1981 | Inagaki et al. . |
| 4,265,252 | 5/1981 | Chubbuck et al. . |
| 4,281,667 | 8/1981 | Cosman . |
| 4,354,506 | 10/1982 | Sakaguchi et al. . |
| 4,378,809 | 4/1983 | Cosman . |
| 4,471,786 | 9/1984 | Inagaki et al. . |
| 4,494,411 | 1/1985 | Koschke et al. . |
| 4,593,703 | 6/1986 | Cosman . |
| 4,653,508 | 3/1987 | Cosman . |
| 4,660,568 | 4/1987 | Cosman . |
| 4,676,255 | 6/1987 | Cosman . |
| 4,738,267 | 4/1988 | Lazorthes et al. . |
| 4,926,696 | 5/1990 | Haritonidis et al. . |
| 5,018,529 | 5/1991 | Tenerz et al. . |
| 5,117,835 | 6/1992 | Mick . |
| 5,260,910 | 11/1993 | Panton . |
| 5,291,899 | 3/1994 | Watanabe et al. . |
| 5,317,917 | 6/1994 | Dufour . |
| 5,361,070 | 11/1994 | McEwan . |
| 5,642,119 | 6/1997 | Jacobs . |
| 5,873,840 | 2/1999 | Neff . |

Primary Examiner—Max Hindenburg
Attorney, Agent, or Firm—Caesar, Rivise, Bernstein, Cohen & Pokotilow, Ltd.

[57] ABSTRACT

A system and method for interrogating implanted passive resonant circuits is described. The resonant frequency is detected by transmitting a train of short pulses and then listening between the pulses for output of the resonant circuit. With proper spacing between the pulses, a vastly improved signal-to-noise ratio is obtained.

20 Claims, 4 Drawing Sheets

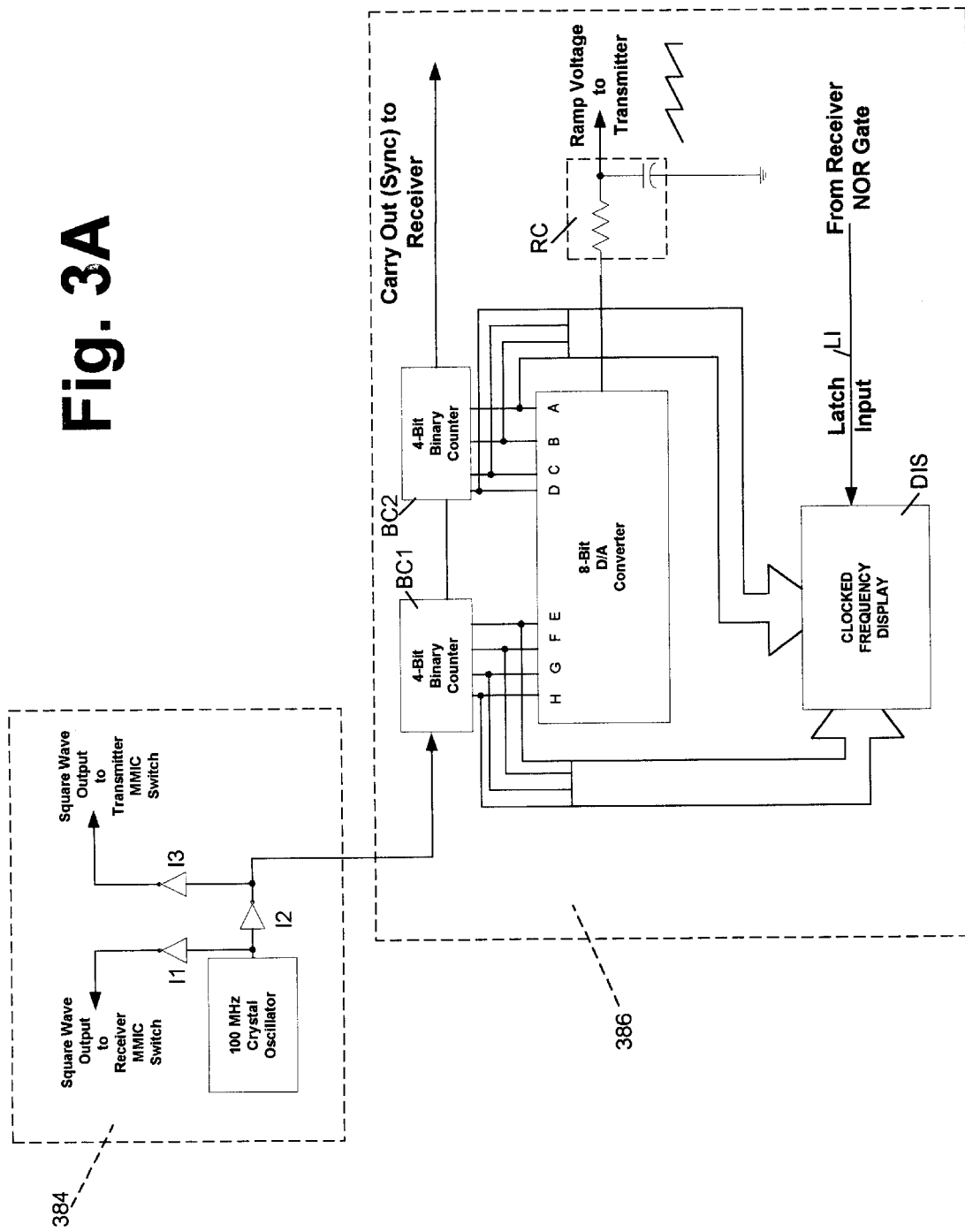

SYSTEM AND METHOD OF INTERROGATING IMPLANTED PASSIVE RESONANT-CIRCUIT DEVICES

SPECIFICATION

BACKGROUND OF THE INVENTION

This invention relates generally to medical devices and more particularly to systems for measuring intracranial pressure, and interrogating other implanted passive resonant circuits.

Numerous patents have been issued disclosing various means for monitoring intracranial pressure by means of an implanted, passive, resonant electronic circuit that is interrogated by an external device.

U.S. Pat. No. 3,943,915 (Severson) discloses an intracranial pressure monitoring device that incorporates a lumped-constant tuned circuit. The typical Q of such a circuit is on the order of 50.

U.S. Pat. No. 4,026,276 (Chubbuck) discloses an intracranial pressure monitoring device with a lumped-constant tuned circuit. The typical Q of such a circuit is on the order of 50.

U.S. Pat. No. 4,114,606 (Seylar) discloses a monitoring device for implanted resonant circuits. They are not able to even estimate the signal-to-noise ratio, but use a "grid-dip meter" approach, i.e., the detector voltage "dips" whenever the interrogating circuit sweeps by the resonant frequency of the implanted resonant frequency circuit.

U.S. Pat. No. 4,265,252 (Chubbuck) discloses an intracranial pressure monitoring device with a lumped-constant tuned circuit.

U.S. Pat. No. 4,354,506 (Sakaguchi) discloses an intracranial pressure monitoring device with a lumped-constant tuned circuit, and purposed using a "grid-dip meter" monitoring system.

U.S. Pat. No. 5,873,840 (Neff) discloses an intracranial pressure sensor with a microwave cavity resonator. The preferred embodiment discussed includes a reflected energy measurement approach.

However, all of these devices suffer from poor signal-to-noise ratios. Thus, there remains a need for an implanted resonant circuit that provides for a response signal with good signal-to-noise ratio when interrogated.

OBJECTS OF THE INVENTION

Accordingly, it is the object of this invention to provide a system and method for determining the resonant frequency of a circuit, lumped-constant or other, implanted in a person.

It is further the object of this invention to provide a system and method that can work over a wide range of frequencies, and uses commercially available components.

It is further the object of this invention to provide a system and method with a high signal-to-noise ratio, which allows it to work without direct contact with the patient.

It is further the object of this invention to provide a system and method that exposes the patient to acceptable levels of irradiation, suitable for continuous monitoring.

It is still yet a further object of this invention to provide a system and method for whose performance is much less sensitive to path loss.

It is even still another object of this invention to provide a system and method for that it is completely insensitive to dispersion (frequency-dependent reflection, absorption, and transmission characteristics) of the tissue.

SUMMARY OF THE INVENTION

These and other objects of the instant invention are achieved by providing a system for monitoring the pressure within the cranium of a living being. The system comprises: a resonant frequency circuit that is implanted within the cranium; a remotely-located transmitter (e.g., a voltage-controlled YIG oscillator) and a remotely-located receiver coupled through alternation means (e.g., a pair of MMIC switches) that operates the transmitter and receiver in alternation such that when the transmitter is transmitting an interrogation signal to the resonant frequency circuit, the remotely-located receiver is de-activated and when the receiver is listening to a response signal from the resonant frequency circuit the transmitter is de-activated; the interrogation signal comprises high frequency electromagnetic excitation waves (e.g., 3.8–3.82 Ghz) wherein one of the excitation waves causes the resonant frequency circuit to resonate at an altered resonance frequency corresponding to the pressure of the cranium; the remotely-located receiver detects the altered resonance frequency in the response signal; and a display, coupled to the remotely-located receiver, displays the pressure of the cranium corresponding to the detected altered resonance frequency.

These and other objects of the instant invention are also achieved by providing a method for monitoring the pressure within the cranium of a living being. The method comprises the steps of: implanting a resonant frequency circuit within the cranium; transmitting high frequency electromagnetic excitation waves (e.g., 3.8–3.82 Ghz) from a transmitter (e.g., a voltage-controlled YIG oscillator) to the resonant frequency circuit while precluding a receiver from receiving any response signal from the resonant frequency circuit during the transmitting and wherein one of the excitation waves causes the resonant frequency circuit to resonate at an altered resonance frequency corresponding to the pressure of the cranium; precluding the transmitter from transmitting the high frequency electromagnetic waves while the receiver receives a response signal from the resonant frequency circuit; detecting the altered resonance frequency in the response signal by the receiver; and displaying the pressure of the cranium corresponding to the detected altered resonance frequency.

DESCRIPTION OF THE DRAWINGS

Other objects and many of the attendant advantages of this invention will be readily appreciated as the same becomes better understood by reference to the following detailed description when considered in connection with the accompanying drawings wherein:

FIG. 3A is a circuit schematic of the timing circuit and the voltage sweeper/pressure display.

DETAILED DESCRIPTION OF THE PREFERRED EMBODIMENT

The present invention is an improvement of the intercranial pressure monitoring system of U.S. Pat. No. 5,873,840 (Neff) whose entire disclosure is incorporated by reference herein.

Figure 1:
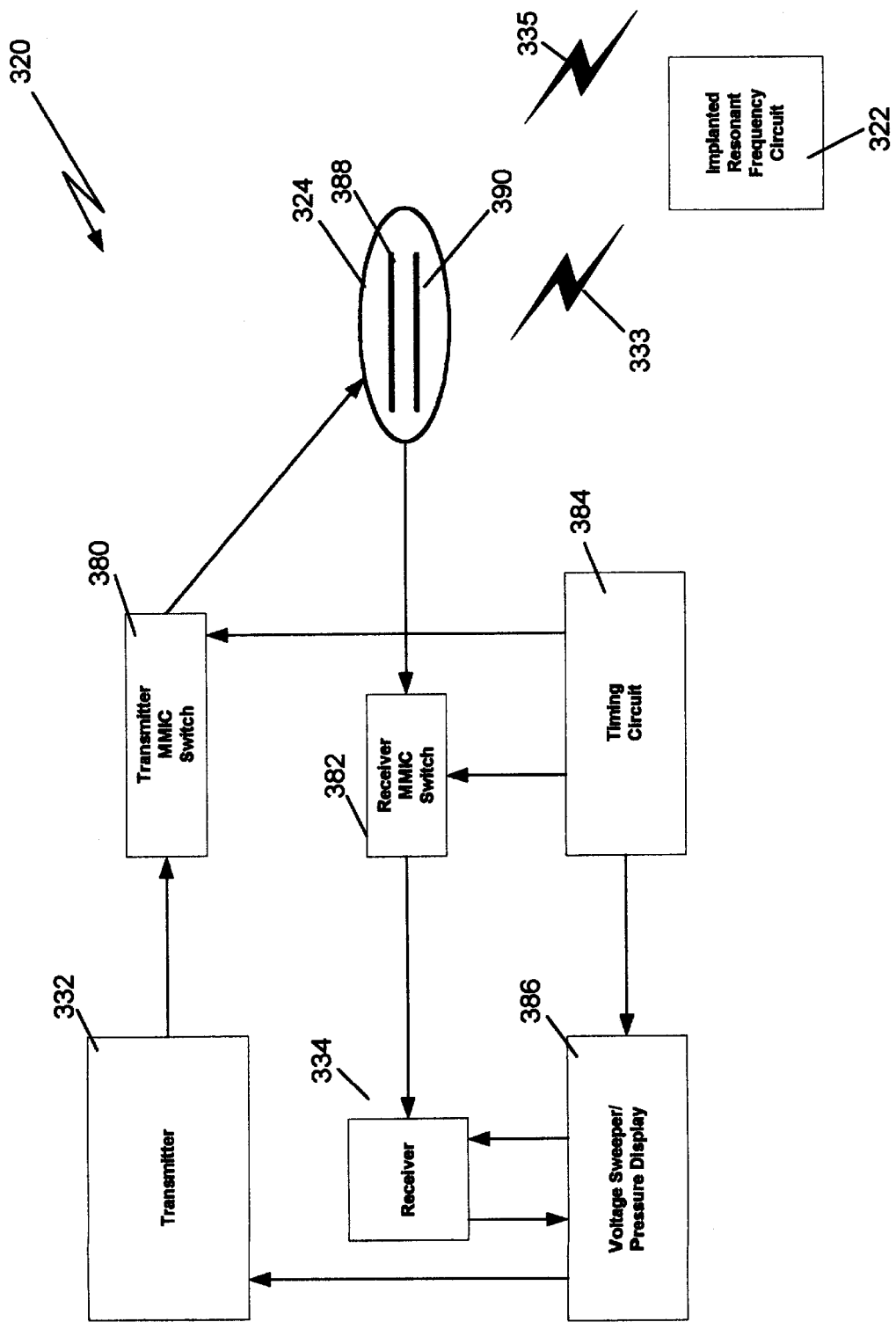
FIG. 1 a block diagram of the present invention.

Referring now in detail to the various figures of the drawing wherein like reference characters refer to like parts, there is shown at 320 in FIG. 1, a system for interrogating an implanted resonant circuit 322 (e.g., the cavity resonator unit 22 of U.S. Pat. No. 5,873,840 (Neff)) that is embedded below the scalp of a patient (not shown). The system 320 comprises a transmitter 332, a receiver 334, a transmit MMIC (monolithic microwave integrated circuit) switch 380, a receive MMIC switch 382, a timing circuit 384 and a voltage sweeper/pressure display (hereinafter referred to as VSPD) 386. The probe 324 comprises a stripline transmit antenna 388 and a stripline receiver antenna 390. When activated, as discussed below, the transmitter MMIC switch 380 permits the transmitter 332 to transmit a signal 333 through the stripline transmit antenna 338; similarly, when the receiver MMIC switch 382 is activated, the receiver MMIC switch 382 permits the receiver 334 to receive a return signal 335 from the implanted resonant frequency circuit 322.

It should be understood that the resonance frequency of the implanted resonant frequency circuit 322 is changed as a function of the patient's cranium pressure. See U.S. Pat. No. 5,873,840 (Neff). Thus, depending upon the cranium pressure, the resonance frequency will change. Furthermore, embedded in the return signal 335 is a peak value signal that corresponds to the resonant frequency. As a result, the phrase "altered resonant wave".

Figure 2:
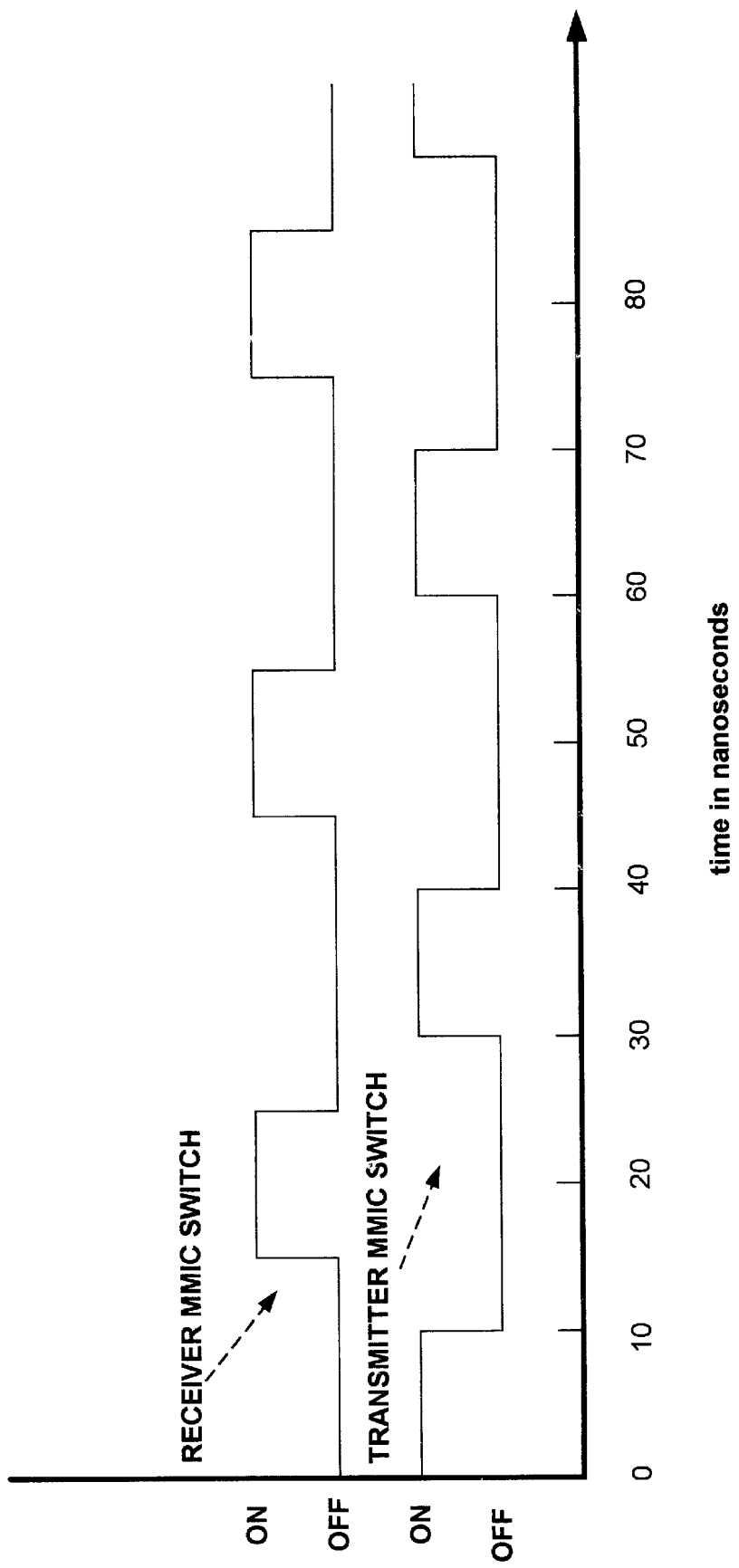
FIG. 2 is a timing diagram of the transmitter and receiver MMIC switches.

The transmitter 332 (e.g., a voltage-controlled YIG (Yitrium iron garnet) oscillator such as the Micro Lambda MLPB-0406 or MLPB-0204) and the receiver 334 are swept in frequency over the range of possible resonant frequencies of the implanted resonant circuit 322. The output signal 333 of the transmitter 332 and the return signal 335 to the receiver 334 are switched synchronously using monolithic GaAs FET MMIC RF switches 380 and 382, respectively, (e.g., Alpha Industries ASO18R-1-00). This synchronous switching effectively disconnects the transmitter 332 when the receiver 334 is on, and effectively disconnects the receiver 334 while the transmitter 332 is on (see FIG. 2). The switches 380/382 are keyed from an oscillator/counter/demultiplexing timing circuit 384 that compensates for the 3 nanosecond switching time of the MMIC switches 380 and 382. The connection between the transmitter 332 and the receiver 334 is loosely coupled (i.e., the transmitter 332/receiver 334 and the implanted resonant frequency circuit are displaced from each other over a finite distance, in addition to the scalp of the patient acting as a lossy dielectric) to the implanted resonant frequency circuit 322.

In particular, the transmitter 332 is slowly swept across the resonant frequency of the implanted resonant frequency circuit 322. The timing circuit 384 alternatively switches the receiver 334 and the transmitter 332 in and out of the system 320. During each pulse from the transmitter 332, the receiver 334 is "off", i.e., disconnected at >80 dB attenuation by the receiver MMIC switch 382. Similarly, during each period when the receiver 334 is "listening," the transmitter 332 is "off." With the transmitter 332 off, the receiver 334 amplifies and detects only the decay of the energy stored in the implanted resonant frequency circuit 322. This energy decay is defined as:

$$e^{\frac{-ft}{Q}}$$

where

F=frequency in Hertz; and

Q=Q factor of implanted resonant frequency circuit 322.

Typical operating values of the system 20 are as follows:

| | |
|---|---|
| Operating frequency of transmitter 332: | 3.8–3.82 Ghz |
| Q of implanted resonant frequency circuit 322: | 8000 |
| Keying waveform for transmitter 332: | 10 ns pulses spaced 20 ns |
| Keying waveform for receiver 334: | 10 ns pulses spaced 20 ns, synchronized 15 ns behind transmitter |
| Total path loss (including coupling to implanted resonant frequency in tissue): | 70 dB |
| Minimum discernable signal of receiver: | −110 dBm |
| Transmitter 332 output: | +10 dBm. |

With these values, the implanted resonant frequency circuit 322 decay is approximated as:

$$(10\,\text{dBm} - 70\,\text{dB}) \cdot e^{\frac{-ft}{Q}} = -60\,\text{dBm} \cdot e^{\frac{-t}{2.1 \times 10^{-6}}}$$

(with t in nano seconds)

In other words, it will take approximately 2.1 μsec for the decay to reach 36.8% (i.e., at t=2.1×10⁻⁶ sec, the decay is given by e⁻¹=0.368) of its initial value (−60 dBm). This means that with the transmitter 332 clocked at 100 MHz (10 ns), very little decay occurs during the next 10 ns when the receiver 334 is "connected." Therefore, the received energy at the start of the receiver MMIC switch 382 "on-time" is −60 dBm, well above the minimum discernable signal (−110 dBm) of the receiver 334. During the "off-time" of the receiver 334, the leakage input from the transmitter 332 is:

−70 dBm −(coupling between transmitter antenna 388 and receiver antenna 390).

Conservatively estimating the coupling of the two parallel stripline antennas 388/390 is at −20 dB, the final value of −90 dBm is 30 dB below the desired signal.

The result of the system 20 and method is that rather than looking for a small change in a large signal, as the grid-dip method requires, the "pulse-detector" operation of the system 20/method only provides an output when at the resonant frequency of the circuit 322. In particular, as will be discussed later, the system 20/method detects the peak value in the return signal 335 which corresponds to the resonant frequency of the implanted resonant frequency circuit 322. The pressure in the patient's cranium that corresponds to that frequency is then displayed to the operator via a display DIS (FIG. 3A).

In comparison, if the "grid-dip" approach, (i.e., without the alternate transmitter/receiver switching) were used, and applying the operating values listed above, the input to the receiver from the transmitter is −10 dBm (in a classic, grid-dip meter the receiver and transmitter are the same circuit, but this does not change the physics). The input from the implanted resonant frequency circuit 322 is −60 dBm, (and even smaller when off-resonance). Thus, the receiver is attempting to detect a change that is 50 dB smaller than the signal itself, or 0.001% of the signal strength. Although it is possible to do this in the laboratory, routine clinical use of such a device is not realistic.

Figure 3B:
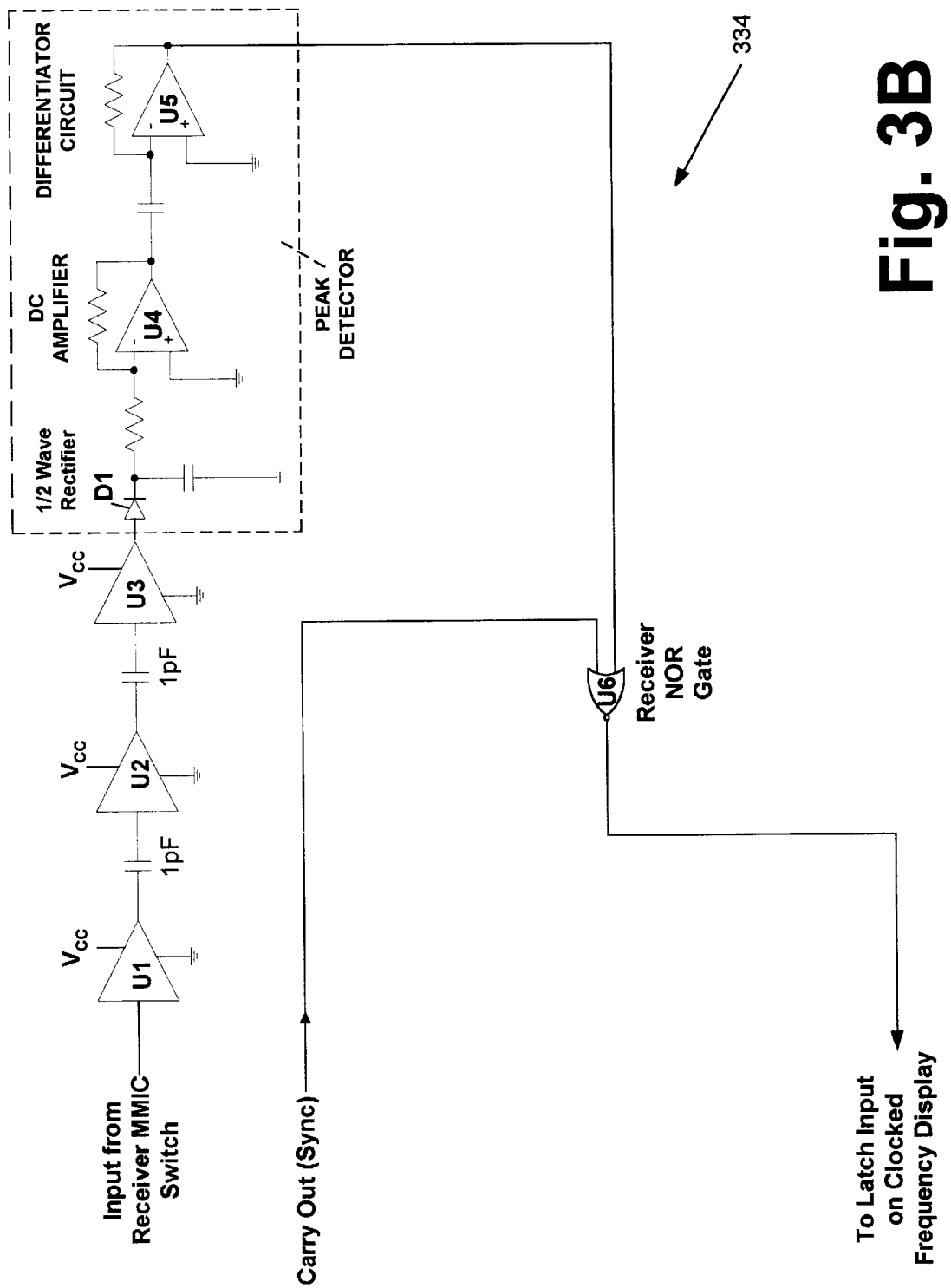
FIG. 3B is a circuit schematic of the receiver.

FIGS. 3A–3B show an exemplary implementation of the timing circuit 384, the VSPD 386 and the receiver 334.

The timing circuit 384 (FIG. 3A) comprises a 100 MHz crystal oscillator (e.g., JDR Microdevices #OSC100.0 oscillator) whose output is fed to inverters I1 and I2 (e.g., Fairchild Semiconductor 74VHC04 Hex inverter). The output of inverter I1 is fed into the receiver MMIC switch 382.

The output of inverter I2 is fed to the VSPD 386 and to another inverter I3 (e.g., Fairchild Semiconductor 74VHC04 Hex inverter). The output of the inverter I3 is fed to the transmitter MMIC switch 380.

The VSPD 386 receives its input from the inverter I3. A pair of 4-bit binary counters BC1 and BC2 (e.g., Fairchild Semiconductor 74VHC93) are incremented by the 100 MHz crystal oscillator signal, from inverter I2, in 256 ($2^8$) increments. The digital incrementation is converted by an 8-bit digital/analog converter (e.g., JDR #DAC-0800) and resistor/capacitor network RC into an analog ramp voltage signal that is used to sweep the oscillator of the transmitter 332 through the pertinent frequency range, e.g., 3.8–3.82 GHz. The ramp voltage signal (see FIG. 3A) exhibits linearly-increasing portions and substantially-vertical re-trace portions. The digital incrementation is simultaneously fed to a clocked frequency display DIS which converts the frequency into the corresponding cranial pressure in the range from 0–30 Torr (mmHg). When the resonant frequency of the implanted circuit 322 is detected by the receiver 334, a latch input signal L1 from the receiver 334 (to be discussed below) is transmitted to the display DIS which latches the frequency value supplied from the binary counters BC1/BC2 and the display DIS then displays the pressure corresponding to that latched frequency value.

The receiver 334 (FIG. 3B) comprises three MMIC amplifiers U1, U2 and U3 (e.g., ERA-3 MMIC amplifiers) connected in series through 1pF coupling capacitors. Input to amplifier U1 is controlled by the receiver MMIC switch 382. Thus, when the receiver MMIC switch 382 is active, the received signal 335 is passed to the input of amplifier U1. The output of amplifier U3 is fed through a peak detector formed by a half-wave rectifier, a DC amplifier U4 and a differentiator circuit U5. The half-wave rectifier comprises a diode D1 (e.g., Hewlett-Packard 5082-2835 diode) coupled to ground through a capacitor. The output of the half-wave rectifier is fed to a DC amplifier U4 (e.g., LM301 op amp) which in turn is fed to a differentiator circuit U5 (e.g., LM301 op amp).

The differentiator circuit U5 provides a zero output under two conditions: (1) when the received signal 335 is at the resonant frequency of the implanted resonant frequency circuit 322 (i.e., at the peaks of the return signal 335); and (2) when the ramp voltage, generated by the VSPD 386, is re-tracing, i.e., the vertical portion of the ramp is occurring. In order for the system 20 to operate properly, it is necessary to distinguish between these two conditions such that the display DIS only displays under condition (1) and not under condition (2). To that end, the output of the differentiator circuit U5 is fed as one input to a receiver NOR gate U6. The other input to the receiver NOR gate U6 is a carry out (sync) signal from binary counter BC2 that corresponds to the re-trace portion of the ramp voltage. Thus, the output of the NOR gate U6 is asserted (i.e., permits latching to the display DIS) only when the differentiator circuit U5 output is zero (which corresponds to a peak in the received signal 335 which corresponds to the received signal 335 being at the resonant frequency) and the ramp voltage is not experiencing a re-trace.

A further advantage of this system 20 and method is that the performance is much less sensitive to path loss. In the exemplary embodiment discussed above the receiver 334 could easily be placed a small (line-of-sight) distance from the patient.

A further advantage of this system and method is that it is completely insensitive to dispersion (frequency-dependent reflection, absorption, and transmission characteristics) of the tissue. Only the implanted resonant frequency circuit 322 provides a signal during the time the receiver 334 is "on."

Without further elaboration, the foregoing will so fully illustrate my invention that others may, by applying current or future knowledge, readily adopt the same for use under various conditions of service.

I claim:

1. A system for monitoring the pressure within the cranium of a living being, said system comprising:

a resonant frequency circuit that is implanted within the cranium;

a remotely-located transmitter and a remotely-located receiver coupled through alternation means that operates said transmitter and receiver in alternation such that when said transmitter is transmitting an interrogation signal to said resonant frequency circuit said remotely-located receiver is de-activated and when said receiver is listening to a response signal from said resonant frequency circuit said transmitter is de-activated;

said interrogation signal comprising high frequency electromagnetic excitation waves wherein one of said excitation waves causes said resonant frequency circuit to resonate at an altered resonance frequency corresponding to the pressure of the cranium;

said remotely-located receiver detecting said altered resonance frequency in said response signal; and a display, coupled to said remotely-located receiver, for displaying the pressure of the cranium corresponding to said detected altered resonance frequency.

2. The system of claim 1 wherein said alternation means comprises:

a timing circuit;

a first switch coupled between said timing circuit and said remotely-located transmitter, said first switch having a first closed state that activates said transmitter and a first open state that de-activates said transmitter;

a second switch coupled between said timing circuit and said remotely-located receiver, said second switch having a second closed state that activates said receiver and a second open state for de-activating said receiver; and said timing circuit closing said first switch in said first closed state while opening said second switch in said second open state and then opening said first switch in said first open state while closing said second switch in said second closed state.

3. The system of claim 2 wherein said first closed state is approximately 10 nanoseconds and said first open state is approximately 20 nanoseconds.

4. The system of claim 2 wherein said second closed state is approximately 10 nanoseconds and said second open state is approximately 20 nanonseconds.

5. The system of claim 3 wherein said first switch is a monolithic microwave integrated circuit.

6. The system of claim 4 wherein said second switch is a monolithic microwave integrated circuit.

7. The system of claim 1 wherein said transmitter comprises a voltage-controlled oscillator (VCO) and wherein said system further comprises a voltage sweeper, said voltage sweeper controlling said VCO to generate said high frequency electromagnetic excitation waves.

8. The system of claim 1 wherein said high frequency electromagnetic excitation waves are in the range of 3.8–3.82 GHz.

9. The system of claim 7 wherein said high frequency electromagnetic excitation waves are in the range of 3.8–3.82 GHz.

10. The system of claim 7 wherein said receiver comprises a peak detector for detecting said altered resonant frequency in said response signal.

11. The system of claim 10 wherein said peak detector comprises a half-wave rectifier, a direct current (DC) amplifier and a differentiator coupled together in series.

12. The system of claim 11 wherein said voltage sweeper generates a ramp voltage for controlling said VCO, said ramp voltage comprising linearly increasing portions and substantially vertical re-trace portions.

13. The system of claim 13 wherein said receiver further comprises logic means having a first input coupled to the output of said differentiator and a second input coupled to said voltage sweeper, said logic means having an output coupled to said display and wherein said logic means decouples said receiver from said display during said re-trace portions of said ramp voltage while permitting said display to display the pressure of the cranium when said altered resonance frequency is detected by said receiver.

14. A method for monitoring the pressure within the cranium of a living being, said method comprising the steps of:
implanting a resonant frequency circuit within the cranium;
transmitting high frequency electromagnetic excitation waves from a transmitter to said resonant frequency circuit while precluding a receiver from receiving any response signal from said resonant frequency circuit during said transmitting and wherein one of said excitation waves causes said resonant frequency circuit to resonate at an altered resonance frequency corresponding to the pressure of the cranium;
precluding said transmitter from transmitting said high frequency electromagnetic waves while said receiver receives a response signal from said resonant frequency circuit;
detecting said altered resonance frequency in said response signal by said receiver; and
displaying the pressure of the cranium corresponding to said detected altered resonance frequency.

15. The method of claim 14 wherein said step of transmitting high frequency electromagnetic excitation waves from a transmitter to said resonant frequency circuit while precluding a receiver from receiving any response signal comprises de-activating said receiver for approximately 20 nanoseconds while activating said transmitter for approximately 10 nanoseconds.

16. The method of claim 15 wherein said step of precluding said transmitter from transmitting said high frequency electromagnetic waves while said receiver receives a response signal comprises de-activating said transmitter for approximately 20 nanoseconds while activating said receiver for approximately 10 nanoseconds.

17. The method of claim 14 wherein said step of transmitting high frequency electromagnetic excitation waves comprises sweeping said transmitter through the frequency range of 3.8–3.82 Ghz.

18. The method of claim 17 wherein step of sweeping said transmitter comprises using a ramp voltage control signal to sweep said transmitter, said ramp voltage control signal comprising linearly-increasing portions and substantially-vertical re-trace portions.

19. The method of claim 14 wherein said step of detecting said altered resonance frequency in said response signal comprises detecting the peak value in said response signal.

20. The method of claim 18 further comprising the step of decoupling said receiver from said display during said re-trace portions of said ramp voltage control signal.

* * * * *